United States Patent [19]  [11] Patent Number: 4,602,943
Yamane et al.  [45] Date of Patent: Jul. 29, 1986

[54] CERTAIN PYRIDYLOXYBENZANILIDES HAVING HERBICIDAL PROPERTIES

[75] Inventors: Izumi Yamane; Mitsumasa Yamazaki; Takeo Motegi; Yasuya Sakuraba, all of Tokyo, Japan

[73] Assignee: Hodogaya Chemical Co., Ltd., Tokyo, Japan

[21] Appl. No.: 564,180

[22] Filed: Dec. 22, 1983

[51] Int. Cl.[4] .................. C07D 213/64; A01N 43/40
[52] U.S. Cl. .......................................... 71/94; 546/291
[58] Field of Search ............................ 546/291; 71/94

[56] References Cited

U.S. PATENT DOCUMENTS 4,302,242  11/1981  Cartwright ............................ 71/94

FOREIGN PATENT DOCUMENTS 0024669  8/1980  European Pat. Off. ............ 544/224
0025363  3/1981  European Pat. Off. ............ 546/291
2091256  8/1982  United Kingdom ................ 546/298

OTHER PUBLICATIONS

Chemical Abstracts, vol. 98, (11) abst. No. 89181d Mar. 14, 1983.

Primary Examiner—Alan L. Rotman
Attorney, Agent, or Firm—Oblon, Fisher, Spivak et al.

[57] ABSTRACT

A pyridyloxybenzanilide derivative represented by the formula:

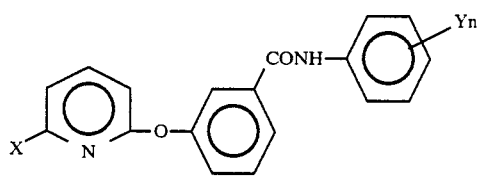

where X is a bromine atom, Y is a halogen atom, a trifluoromethyl group, a trifluoromethoxy group, a lower alkyl group or a lower alkoxy group, and n is an integer of from 1 to 3.

14 Claims, No Drawings

CERTAIN PYRIDYLOXYBENZANILIDES HAVING HERBICIDAL PROPERTIES

The present invention relates to a novel pyridyloxybenzanilide derivative and a herbicide containing it.

The present inventors have conducted extensive researches on the herbicidal activities of pyridyloxy benzoic acid-type compounds and have found that certain specific pyridyloxybenzanilide derivatives have characteristic herbicidal activities. The present invention is based on this discovery.

Namely, the present invention provides a pyridyloxybenzanilide derivative represented by the general formula:

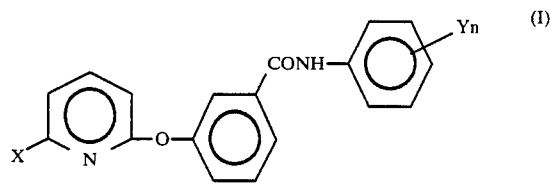

where X is a bromine atom, Y is a halogen atom, a trifluoromethyl group, a trifluoromethoxy group, a lower alkyl group or a lower alkoxy group, and n is an integer of from 1 to 3.

Now, the present invention will be described with reference to the preferred embodiments.

In the general formula I, Y is a halogen atom such as fluorine, chlorine or bromine; a trifluoromethyl group; a trifluoromethoxy group; a lower alkyl group such as methyl, ethyl, propyl or isopropyl; or a lower alkoxy group such as methoxy, ethoxy or propoxy.

Representative pyridyloxybenzanilide derivatives of the present invention are shown in Table 1.

TABLE 1

| Compound No. | Chemical formulas | Melting point (°C.) |
|---|---|---|
| 1 | (structure with Br-pyridine-O-phenyl-CONH-phenyl-F) | 113–115 |
| 2 | (structure with Br-pyridine-O-phenyl-CONH-phenyl-Cl) | 94–96 |
| 3 | (structure with Br-pyridine-O-phenyl-CONH-phenyl-Br) | 100–104 |
| 4 | (structure with Br-pyridine-O-phenyl-CONH-phenyl-CH₃) | 125–126 |
| 5 | (structure with Br-pyridine-O-phenyl-CONH-phenyl-C₂H₅) | 121–123 |

TABLE 1-continued

| Compound No. | Chemical formulas | Melting point (°C.) |
|---|---|---|
| 6 | Br-pyridyl-O-phenyl-CONH-phenyl(2-CH(CH₃)₂) | 112-115 |
| 7 | Br-pyridyl-O-phenyl-CONH-phenyl(2-CF₃) | 107-110 |
| 8 | Br-pyridyl-O-phenyl-CONH-phenyl(3-Cl) | 125-128 |
| 9 | Br-pyridyl-O-phenyl-CONH-phenyl(3-CH₃) | 129-133 |
| 10 | Br-pyridyl-O-phenyl-CONH-phenyl(3-CF₃) | 121-125 |
| 11 | Br-pyridyl-O-phenyl-CONH-phenyl(4-F) | 104-108 |
| 12 | Br-pyridyl-O-phenyl-CONH-phenyl(4-CF₃) | 109-112 |

The compounds of the present invention may be prepared, for instance, by the following two processes.

The first process comprises reacting an acid chloride, i.e. a reactive derivative, of 3-(2-bromopyridyloxy)benzoic acid with a substituted aniline in the presence of from 1 to 4 molar times, preferably from 1 to 2 molar times, of a suitable base e.g. an organic base such as triethyl amine or pyridine, or an inorganic base such as sodium hydrogencarbonate or sodium carbonate. This process is preferably conducted in the presence of an inert solvent. The solvent is not critical so long as it does not interfere with the main reaction. For instance, an aromatic hydrocarbon such as benzene or toluene, an alkyl halide such as methylene chloride or chloroform, a ketone such as acetone, or an ether such as tetrahydrofuran or dioxane, may preferably be used. The reaction temperature is not critical, and the reaction is usually conducted at a temperature from 0° C. to the refluxing temperature of the solvent. Particularly preferred is a temperature around room temperature. The reaction time varies depending mainly on the reaction temperature and the type of the reagents used. However, the reaction time is usually from 30 minutes to 3 hours.

The second process comprises reacting 3-hydroxybenzoic acid-substituted anilide with from 1 to 3 molar times, preferably from 1 to 1.5 molar times, of 2,6-dibromopyridine in the presence of from 1 to 6 molar times, preferably from 1 to 3 molar times, of a suitable base, e.g. an inorganic base such as potassium carbonate, sodium carbonate, calcium hydroxide or sodium hydroxide. The reaction is preferably conducted in a solvent, for example, an ether such as dioxane or a polar aprotic solvent such as N,N-dimethylamide or dimethylsulfoxide. The reaction temperature is not critical and is usually from 50° to 200° C., preferably from 100° to 150° C. The reaction time varies depending mainly on the reaction temperature and the type of the reagents used and is usually from 2 to 6 hours.

After the completion of the reaction, the desired compound can be readily separated from the reaction mixture by a usual method.

Now, Synthetic Examples for the preparation of the compounds of the present invention will be described.

SYNTHETIC EXAMPLE 1 (SYNTHESIS OF COMPOUND NO. 2)

3-(6-Bromo-2-pyridyloxy)benzoic acid-2'-chloroanilide 2.55 g of 2-chloroaniline and 2.42 g of triethylamine were dissolved in 100 ml of tetrahydrofuran. While cooling the solution to a temperature of not higher than 5° C., 6.33 g of 3-(6-bromo-2-pyridyloxy)benzoic acid chloride was added. After the addition, the mixture was stirred for 2 hours, and then tetrahydrofuran was recovered under reduced pressure. A dilute hydrochloric acid aqueous solution was added to the residue, and the precipitated crystals were collected by filtration and dried to obtain 7.60 g of 3-(6-bromo-2-pyridyloxy)benzoic acid-2'-chloroanilide. The yield was 93.2%, and the melting point was from 94° to 96° C.

SYNTHETIC EXAMPLE 2 (SYNTHESIS OF COMPOUND NO. 4)

3-(6-Bromo-2-pyridyloxy)benzoic acid-2'-methylanilide 2.14 g of orthotoluidine was dissolved in 50 ml of dioxane, and 2.52 g of sodium hydrogencarbonate was added. While thoroughly stirring the mixture, 6.33 g of 3-(6-bromo-2-pyridyloxy)benzoic acid chloride dissolved in 20 ml of dioxane, was dropwise added at room temperature. After the dropwise addition, the mixture was stirred at room temperature for 3 hours, and then poured into a dilute hydrochloric acid aqueous solution. The precipitated crystals were collected by filtration, washed with water and then dried to obtain 7.01 g of 3-(6-bromo-2-pyridyloxy)benzoic acid-2'-methylanilide. The yield was 90.6%, and the melting point was from 125° to 126° C.

SYNTHETIC EXAMPLE 3 (SYNTHESIS OF COMPOUND NO. 5)

3-(6-Bromo-2-pyridyloxy)benzoic acid-2'-ethylanilide

The reaction was conducted in the same manner as in Synthetic Example 1 by using 2.42 g of 2-ethylaniline instead of 2-chloroaniline, whereby 7.23 g of 3-(6-bromo-2-pyridyloxy)benzoic acid-2'-ethylanilide was obtained. The yield was 91.1%, and the melting point was from 121° to 123° C.

SYNTHETIC EXAMPLE 4 (SYNTHESIS OF COMPOUND NO. 6)

3-(6-Bromo-2-pyridyloxy)benzoic acid-2'-isopropylanilide

The reaction was conducted in the same manner as in Synthetic Example 1 by using 2.70 g of 2-isopropylaniline instead of 2-chloroaniline, whereby 6.99 g of 3-(6-bromo-2-pyridyloxy)benzoic acid-2'-isopropylanilide was obtained. The yield was 85.1%, and the melting point was from 117° to 120° C.

SYNTHETIC EXAMPLE 5 (SYNTHESIS OF COMPOUND NO. 9)

3-(6-Bromo-2-pyridyloxy)benzoic acid-3'-methylanilide 4.54 g of 3-hydroxybenzoic acid-3'-methylanilide and 4.74 g of 2,6-dibromopyridine were dissolved in 80 ml of dimethylformamide, and 5.52 g of potassium carbonate was added. The mixture was stirred under heating at 130° C. for 4 hours. After cooling, the reaction product was poured into a 3% sodium hydroxide aqueous solution. The precipitated crystals were collected by filtration, washed with a dilute hydrochloric acid aqueous solution and further with water, and then dried to obtain 6.44 g of 3-(6-bromo-2-pyridyloxy)benzoic acid-3'-methylanilide. The yield was 84.1%, and the melting point was from 129° to 133° C.

SYNTHETIC EXAMPLE 6 (SYNTHESIS OF COMPOUND NO. 11)

3-(6-Bromo-2-pyridyloxy)benzoic acid-4'-fluoroanilide

The reaction was conducted in the same manner as in Synthetic Example 5 by using 4.62 g of 3-hydroxybenzoic acid-4'-fluoroanilide instead of 3-hydroxybenzoic acid-3'-methylanilide, whereby 6.66 g of 3-(6-bromo-2-pyridyloxy)benzoic acid-4'-fluoroanilide was obtained. The yield was 86.1%, and the melting point was from 104° to 108° C.

According to the second aspect of the present invention, a herbicide is prepared by mixing a compound of the present invention as the active ingredient with various carriers to obtain various formulations such as a wettable powder, an emulsifiable concentrate, a dust or a granule. As liquid carriers, ordinary organic solvents may be used, and as solid carriers, ordinary fine mineral powders may be used. Further, a surfactant may be incorporated to improve the emulsifiability, dispersibility or extendability of the formulations. It is also possible to incorporate other agricultural chemicals such as fertilizer, a herbicide, an insecticide, a fungicide or a bactericide.

When used as a herbicide, the active compound is applied in a sufficient amount to obtain a desired herbicidal activity. The amount of the application, i.e. the dose, is usually from 10 to 1000 g/10 a, preferably from 50 to 500 g/10 a, as the active ingredient. Depending upon its particular use, the active ingredient is formulated in various forms such as an emulsifiable concentrate, a wettable powder, a dust or a granule.

To prepare an emulsifiable concentrate, the active ingredient is dissolved in an agriculturally acceptable organic solvent, and a solvent-soluble emulsifier is added thereto. A suitable solvent is usually immiscible with water, and it is usually an organic solvent such as a hydrocarbon, a chlorinated hydrocarbon, a ketone, an ester, an alcohol or an amide.

As a useful solvent, there may be mentioned toluene, xylene, naphtha, perchloroethylene, cyclohexane, isophorone and dimethylformamide, or a mixture thereof. Particularly preferred solvents are aromatic hydrocarbons and ketones. It is common to employ a mixture of solvents.

When used as an emulsifier, a surfactant is usually incorporated in an amount of from 0.5 to 20 parts by weight relative to the emulsifiable concentrate, and the surfactant may be anionic, cationic or nonionic.

The anionic surfactant includes alcohol sulfates or sulfonates, or alkylarylsulfonates or sulfosuccinates, such as calcium dodecylbenzene sulfonate or sodium dioctyl sulfosuccinate.

The cationic surfactant includes aliphatic alkylamine salts and aliphatic alkyl quaternary salts, such as laurylamine hydrochloride or lauryldimethylbenzyl ammonium chloride.

As the useful nonionic emulsifier, there may be mentioned alkylphenols, aliphatic alcohols, mercaptan or ethyleneoxide adducts of fatty acids, such as a polyethylene glycol ester of stearic acid or a polyethylene glycol ether of palmityl alcohol or octylphenol.

The concentration of the active ingredient is usually from 5 to 80 parts by weight, preferably from 10 to 60 parts by weight.

The wettable powder is usually prepared by adding the active ingredient to an inert fine solid carrier and a surfactant. The active ingredient is usually incorporated in an amount of from 10 to 80 parts by weight, and the surfactant is usually incorporated in an amount of from 0.5 to 20 parts by weight.

As the solid carrier commonly employed for the combination with the active ingredient, there may be mentioned naturally produced clay, silicate or silica, or lime, a carbonate or an organic carrier. The typical representatives include kaolin, Zeeklite, fuller's earth, talc, diatom earth, magnesium lime, dolomite and kernel powder.

As a commonly employed surfactant, there may be mentioned a polyoxyethylene-modified alkylphenol, an aliphatic alcohol, a fatty acid, an alkylamine, an alkyaryl sulfonate, a dialkylsulfosuccinate, a sodium salt of a copolymer of maleic anhydride with diisobutylene, sodium lignin sulfonate or formaldehyde-sodium naphthalene sulfonate.

A granule may be prepared by mixing the active ingredient with a granular or pelletized agricultually acceptable carrier, for instance, bentonite, kaolin clay, diatom earth or talc having a particle size of from 8 to 60 mesh. In many cases, a surfactant or a water soluble inorganic salt may be added to improve the disintegrating property.

The herbicide of the present invention is effective mainly for the inhibition of germination and growth of weeds. It exhibits a superior herbicidal activity not only against barnyardgrass (*Echinochloa crusgalli*) as the major weed in the rice field, but also against annual broad leaf weeds such as monochoria (*M. vaginalis* (BURM fil.) PRESL), rotala (*R. indica* KOEHNE), waterwort (*Elatine triandra*) and fatse pimpernel (*L. pyxidaria* LINN) and other weeds such as umbrella plant (*C. difformis* LINN). Yet, it does not give any phytotoxicity to transplanted rice. It is a herbicide having high selectivity. Further, it exhibits not only a high herbicidal activity as a pre-emergence herbicide for upland field but also a herbicidal activity in the post-emergence treatment, and thus it is a herbicide having a wide usage of herbicidal activities.

Now, specific Examples for the preparation of the herbicides of the present invention will be described. In these Examples, "parts" means "parts by weight".

FORMULATION EXAMPLE 1 (emulsifiable concentrate)

Compound No. 2: 10 parts
Xylene: 50 parts
Cyclohexanone: 30 parts
Sorpol 800-A (tradename, manufactured by Toho Chemical Co. Ltd.): 10 parts The above ingredients were homogeneously mixed and dissolved to obtain an emulsifiable concentrate of the present invention.

FORMULATION EXAMPLE 2 (wettable powder)

Compound No. 5: 20 parts
Kaolin clay: 70 parts
White carbon: 5 parts
Sorpol 5039: 5 parts The above ingredients were mixed and pulverized to obtain a wettable powder of the present invention.

FORMULATION EXAMPLE 3 (granule)

Compound No. 9: 5 parts
Bentonite: 45 parts
Talc: 44 parts
Sodium lignin sulfonate: 5 parts
Dialkylsulfosuccinate: 1 part The above ingredients were homogeneously mixed and ·pulverized, and after the addition of water, kneaded, granulated and dried to obtain a granule of the present invention.

TEST EXAMPLE 1 (PRE-EMERGENCE TREATMENT IN PADDY FIELD CONDITION)

In a pot of 150 cm$^2$, soil was put, then covered with soil containing seeds of various paddy field weeds i.e. barnyardgrass (*Echinochloa crusgalli*), monochoria (*M. vaginalis* (BURM fil.) PRESL), rotala (*R. indica* KOEHNE) and umbrella plant (*C. difformis* LINN), fertilized, plowed and irrigated to a depth of water of 3 cm. Two rice seedlings (variety: Nihonbare, 2.5 leaf stage) were transplanted. On the 2nd day after the transplantation of the rice seedlings, a predetermined amount of the herbicide of the present invention diluted with water, was dropwise added to the water in the pot by means of a pipette.

On the 30th day after the application of the herbicide, the herbicidal effects and the phytotoxicity to the rice plants were examined.

The results thereby obtained are shown in Table 2. The evaluation was made in accordance with the following evaluation standards.

| Herbicidal index | Phytotoxicity index |
|---|---|
| 5: 100% herbicidal effect | 0: No phytotoxicity |
| 4: 80% herbicidal effect | 1: Slight phytotoxicity |
| 3: 60% herbicidal effect | 2: Moderate phytotoxicity |
| 2: 40% herbicidal effect | 3: Substantial phytotoxicity |
| 1: 20% herbicidal effect | 4: Great phytotoxicity |
| 0: 0% herbicidal effect | 5: Completely killed |

TEST EXAMPLE 2 (PRE-EMERGENCE TREATMENT IN UPLAND CONDITION)

In a box-shaped pot of 400 cm², soil was put, seeded with seeds of soybean, upland rice and wheat, then covered with soil containing seeds of weeds i.e. crabgrass (*D. sanguinalis*), livid amaranth (*Amaranthus Lividus* L) and common lambsquaters (*Chenopodium album*) in a thickness of 1 cm, and, after moderately pressing the soil surface, uniformly watered.

A day after the seeding, the herbicide of the present invention diluted with water was uniformly applied to the soil surface in an amount of 50 l/a.

On the 30th day after the application of the herbicide, the herbicidal effects and the phytotoxicity were evaluated in accordance with the evaluation standards of Test Example 1.

The results thereby obtained are shown in Table 3.
Test Example 3 (Post-emergence treatment)

In a box-shaped pot of 400 cm², soil was put, and seeds of upland rice, wheat, tomator, crabgrass, livid amaranth and common lambsquarters were sown. After the seeding, the plants were grown in a green house, and when the wheat, upland rice, crabgrass, livid amavanth and common lambsquarters reached 4, 2, 2–2.5, 1–2 and 1–2 leaf stages, respectively, a diluted solution of the herbicide of the present invention having a predetermined concentration, was sprayed uniformly to the foliages of the plants in an amount of 20 l/a.

On the 30th day after the spraying, the herbicidal effects and the phytotoxicity were evaluated in accordance with the evaluation standards of Test Example 1.

The results thereby obtained are shown in Table 4.

TEST EXAMPLE 4 (EARLY POST-EMERGENCE TREATMENT IN PADDY FIELD CONDITION)

In a Wagner pot of 200 cm², soil was put, then covered with a soil containing seeds of barnyardgrass, monochoria, votala and umbrella plant, in a thickness of 0.5 cm and irrigated. On the 2nd day after the irrigation, the surface layer was plowed, and, on the 2nd day after the plowing, two rice seedlings of 2-leaf stage were transplanted at two locations. When the barnyard grass reached 1-leaf stage i.e. when other weeds were in the initial stage of germination, a predetermined amount of a 5% granular herbicide of the present invention was uniformly applied manually.

On the 30th day after the application, the herbicidal effects and the phytotoxicity were evaluated in accordance with the evaluation standards of Test Example 1. The results thereby obtained are shown in Table 5.

TABLE 2

| Compound No. | Dose of active ingredient (g/a) | Paddy field treatment — Response of plants | | | | |
|---|---|---|---|---|---|---|
| | | Transplanted rice plant | Barnyardgrass | Monochoria | Rotala | Umbrella plant |
| 1 | 10 | 0 | 2 | 3 | 3 | 3 |
| | 30 | 0 | 4 | 5 | 5 | 5 |
| 2 | 10 | 0 | 5 | 5 | 5 | 5 |
| | 30 | 0 | 5 | 5 | 5 | 5 |
| 3 | 10 | 0 | 5 | 5 | 5 | 4 |
| | 30 | 0 | 5 | 5 | 5 | 5 |
| 4 | 10 | 0 | 5 | 5 | 5 | 5 |
| | 30 | 0 | 5 | 5 | 5 | 5 |
| 5 | 10 | 0 | 5 | 5 | 5 | 5 |
| | 30 | 0 | 5 | 5 | 5 | 5 |
| 6 | 10 | 0 | 4 | 4.5 | 4 | 2 |
| | 30 | 0 | 5 | 5 | 5 | 5 |
| 7 | 10 | 0 | 1 | 2 | 1 | 1 |
| | 30 | 0 | 2 | 3 | 3 | 3 |
| 8 | 10 | 0 | 1 | 4 | 4 | 3 |
| | 30 | 0 | 3 | 5 | 5 | 5 |
| 9 | 10 | 0 | 2 | 4.5 | 4.5 | 4 |
| | 30 | 0 | 4 | 5 | 5 | 5 |
| 10 | 10 | 0 | 0 | 4.5 | 4.5 | 2 |
| | 30 | 0 | 2 | 5 | 5 | 5 |
| 11 | 10 | 0 | 2 | 4 | 4 | 3 |
| | 30 | 0 | 4 | 5 | 5 | 5 |
| 12 | 10 | 0 | 1 | 4.5 | 4.5 | 2 |
| | 30 | 0 | 3 | 5 | 5 | 5 |

TABLE 3

| Compound No. | Dose of active ingredient (g/a) | Upland treatment — Response of plants | | | | | |
|---|---|---|---|---|---|---|---|
| | | Upland rice plant | Soybean | Wheat | Crabgrass | Livid amaranth | Common lambsquarters |
| 1 | 10 | 0 | 0 | 0 | 1 | 2 | 1 |
| | 30 | 0 | 0 | 0 | 3 | 3 | 3 |
| 2 | 10 | 0 | 0 | 0 | 2 | 2 | 2 |
| | 30 | 0 | 0 | 0 | 4 | 5 | 4.5 |
| 3 | 10 | 0 | 0 | 0 | 1 | 5 | 4.5 |
| | 30 | 0 | 0 | 0 | 3 | 5 | 5 |
| 4 | 10 | 0 | 0 | 0 | 3 | 5 | 5 |
| | 30 | 0 | 1 | 0 | 4.5 | 5 | 5 |
| 5 | 10 | 0 | 0 | 0 | 4 | 5 | 5 |
| | 30 | 0 | 0 | 0 | 5 | 5 | 5 |
| 6 | 10 | 0 | 0 | 0 | 3 | 5 | 5 |
| | 30 | 0 | 0 | 1 | 4.5 | 5 | 5 |
| 7 | 10 | 0 | 0 | 0 | 0 | 2 | 2 |
| | 30 | 0 | 0 | 0 | 2 | 3 | 3 |
| 8 | 10 | 0 | 0 | 0 | 0 | 1 | 1 |
| | 30 | 0 | 0 | 0 | 2 | 3 | 2 |
| 9 | 10 | 0 | 0 | 0 | 0 | 1 | 1 |
| | 30 | 0 | 0 | 0 | 2 | 3 | 3 |
| 10 | 10 | 0 | 0 | 0 | 0 | 0 | 0 |
| | 30 | 0 | 0 | 0 | 1 | 2 | 2 |
| 11 | 10 | 0 | 0 | 0 | 0 | 0 | 1 |
| | 30 | 0 | 0 | 0 | 1 | 3 | 3 |
| 12 | 10 | 0 | 0 | 0 | 0 | 1 | 0 |
| | 30 | 0 | 0 | 0 | 1 | 2 | 2 |

TABLE 4

| Compound No. | Dose of active ingredient (%) | Foliage treatment — Response of plants | | | | | |
|---|---|---|---|---|---|---|---|
| | | Upland rice plant | Wheat | Tomato | Crabgrass | Livid amaranth | Common lambsquarters |
| 1 | 0.05 | 0 | 0 | 5 | 1 | 4 | 4 |
| | 0.1 | 0 | 0 | 5 | 1 | 5 | 5 |
| 2 | 0.05 | 0 | 0 | 1 | 0 | 3 | 3 |
| | 0.1 | 0 | 0 | 2 | 1 | 4.5 | 4 |
| 3 | 0.05 | 0 | 0 | 5 | 1 | 4 | 3 |
| | 0.1 | 0 | 1 | 5 | 3 | 5 | 5 |
| 4 | 0.05 | 0 | 0 | 5 | 1 | 4 | 3 |
| | 0.1 | 0 | 0 | 5 | 1 | 5 | 5 |
| 5 | 0.05 | 0 | 0 | 5 | 3 | 5 | 5 |
| | 0.1 | 0 | 0 | 5 | 5 | 5 | 5 |
| 6 | 0.05 | 0 | 0 | 5 | 1 | 3 | 3 |
| | 0.1 | 0 | 0 | 5 | 2 | 5 | 4.5 |
| 7 | 0.05 | 0 | 0 | 5 | 1 | 3 | 3 |
| | 0.1 | 0 | 0 | 5 | 3 | 5 | 5 |
| 8 | 0.05 | 0 | 0 | 4.5 | 2 | 4 | 4 |
| | 0.1 | 0 | 0 | 5 | 4 | 5 | 5 |

TABLE 4-continued

Foliage treatment

| Compound No. | Dose of active ingredient (%) | Upland rice plant | Wheat | Tomato | Crabgrass | Livid amaranth | Common lambsquarters |
|---|---|---|---|---|---|---|---|
| 9 | 0.05 | 0 | 1 | 5 | 4.5 | 4.5 | 4.5 |
|   | 0.1 | 2 | 3 | 5 | 5 | 5 | 5 |
| 10 | 0.05 | 0 | 0 | 5 | 2 | 4 | 3 |
|   | 0.1 | 0 | 0 | 5 | 3 | 5 | 5 |
| 11 | 0.05 | 0 | 0 | 5 | 1 | 5 | 5 |
|   | 0.1 | 0 | 0 | 5 | 3 | 5 | 5 |
| 12 | 0.05 | 0 | 0 | 5 | 1 | 5 | 5 |
|   | 0.1 | 0 | 0 | 5 | 3 | 5 | 5 |

TABLE 5

Early post-emergence treatment with granular herbicide in paddy field

| Compound No. | Granular herbicide (kg/a) | Transplanted rice plant | Barnyard grass | Monochoria | Rotala | Umbrella plant |
|---|---|---|---|---|---|---|
| 2 | 0.3 | 0 | 4.5 | 5 | 5 | 5 |
|   | 0.4 | 0 | 5 | 5 | 5 | 5 |
|   | 0.6 | 0 | 5 | 5 | 5 | 5 |
| 3 | 0.3 | 0 | 4.5 | 5 | 5 | 4 |
|   | 0.4 | 0 | 5 | 5 | 5 | 5 |
|   | 0.6 | 0 | 5 | 5 | 5 | 5 |
| 4 | 0.3 | 0 | 5 | 5 | 5 | 5 |
|   | 0.4 | 0 | 5 | 5 | 5 | 5 |
|   | 0.6 | 0 | 5 | 5 | 5 | 5 |
| 5 | 0.3 | 0 | 5 | 5 | 5 | 5 |
|   | 0.4 | 0 | 5 | 5 | 5 | 5 |
|   | 0.6 | 0 | 5 | 5 | 5 | 5 |
| 9 | 0.3 | 0 | 4.5 | 5 | 5 | 4.5 |
|   | 0.4 | 0 | 5 | 5 | 5 | 4.5 |
|   | 0.6 | 0 | 5 | 5 | 5 | 5 |

We claim:

1. A pyridyloxybenzanilide derivative represented by the formula:

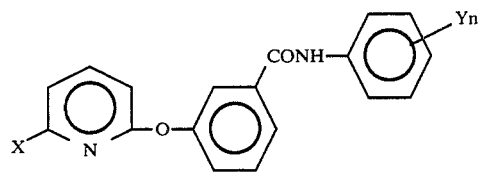

where X is a bromine atom, Y is a halogen atom, a trifluoromethyl group, a trifluoromethoxy group or a lower alkyl group and n is an integer of from 1 to 3.

2. The pyridyloxybenzanilide derivative according to claim 1, which is represented by the formula:

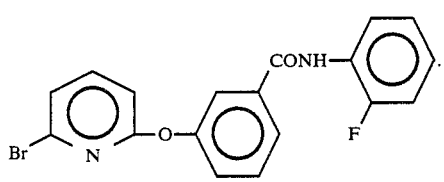

3. The pyridyloxybenzanilide derivative according to claim 1, which is represented by the formula:

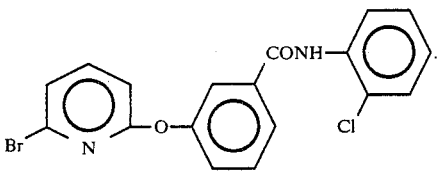

4. The pyridyloxybenzanilide derivative according to claim 1, which is represented by the formula:

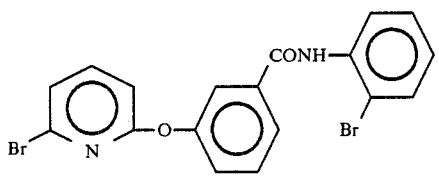

5. The pyridyloxybenzanilide derivative according to claim 1, which is represented by the formula:

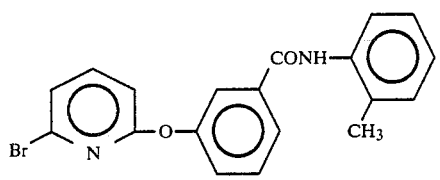

6. The pyridyloxybenzanilide derivative according to claim 1, which is represented by the formula:

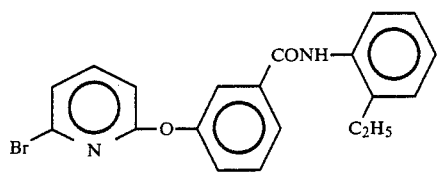

7. The pyridyloxybenzanilide derivative according to claim 1, which is represented by the formula:

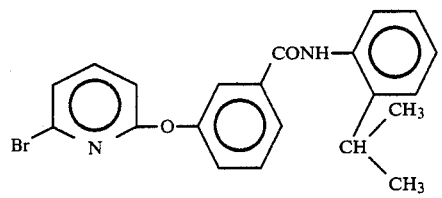

8. The pyridyloxybenzanilide derivative according to claim 1, which is represented by the formula:

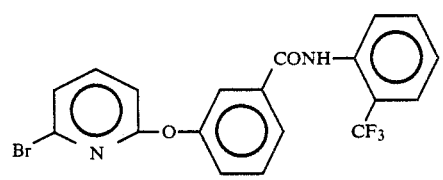

9. The pyridyloxybenzanilide derivative according to claim 1, which is represented by the formula:

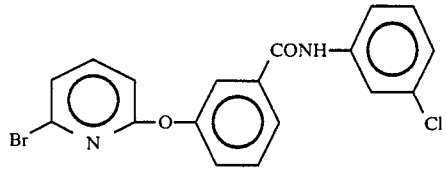

10. The pyridyloxybenzanilide derivative according to claim 1, which is represented by the formula:

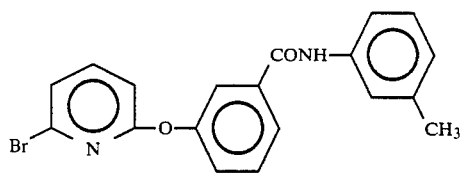

11. The pyridyloxybenzanilide derivative according to claim 1, which is represented by the formula:

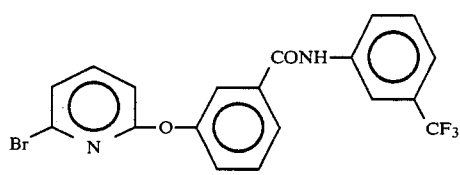

12. The pyridyloxybenzanilide derivative according to claim 1, which is represented by the formula:

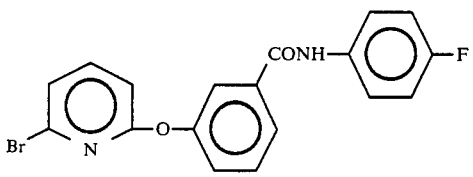

13. The pyridyloxybenzanilide derivative according to claim 1, which is represented by the formula:

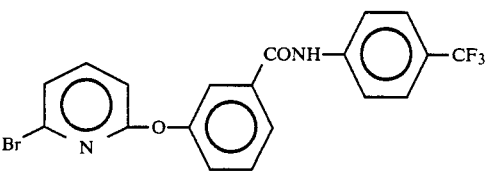

14. A herbicidal composition comprising an effective amount of a pyridyloxybenzanilide derivative represented by the formula:

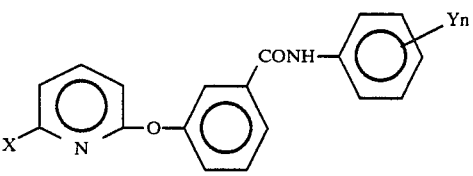

wherein X is a bromine atom, Y is a halogen atom, a trifluoromethyl group, a trifluoromethoxy group or a lower alkyl group, and n is an integer from 1 to 3, and an inert herbicidal carrier.

* * * * *